US005616460A

United States Patent [19]

Figard

[11] Patent Number: 5,616,460
[45] Date of Patent: Apr. 1, 1997

[54] BUFFER COMPOSITION FOR REAGENTS FOR IMMUNOASSAY

[75] Inventor: Steve D. Figard, Zion, Ill.

[73] Assignee: Abbott Laboratories, Abbott Park, Ill.

[21] Appl. No.: 482,710

[22] Filed: Jun. 7, 1995

[51] Int. Cl.[6] .......................... C12Q 1/70; G01N 33/53; G01N 33/543; G01N 33/544
[52] U.S. Cl. .................... 435/5; 435/7.1; 435/7.9; 435/7.92; 435/7.93; 435/7.94; 436/518; 436/528; 436/531; 436/533; 436/820; 436/826; 530/403
[58] Field of Search ..................... 435/5, 7.1, 7.9, 435/7.92, 7.93, 7.94; 436/518, 528, 531, 533, 820, 826; 530/403

[56] References Cited

U.S. PATENT DOCUMENTS

| | | | |
|---|---|---|---|
| 4,956,274 | 9/1990 | Khanna et al. | 435/7 |
| 5,075,221 | 12/1991 | Mauck et al. | 435/7.36 |
| 5,358,691 | 10/1994 | Clark et al. | 422/64 |

FOREIGN PATENT DOCUMENTS

| | | |
|---|---|---|
| 0286367 | 10/1988 | European Pat. Off. . |
| 0363105 | 4/1990 | European Pat. Off. . |
| 2193500 | 7/1987 | United Kingdom . |
| 9306247 | 9/1992 | WIPO . |

OTHER PUBLICATIONS

Patent Abstracts of Japan, vol. 009, No. 066 (C–271), Mar. 26, 1985 & JPA, 59, 198999 (Denka Seiken KK), Nov. 10, 1984.

Database WPI, Section Ch, Week 9027, Derwent Publications Ltd., London, GB, Class A96, An 90–209622, XP002014878, A 9 006 127 (Otsuka Pharm KK), Jun. 14, 1990.

"Cleland's Reagent", Calbiochem–Novabiochem Corporation, San Diego, CA.

Selby, et al., "Expression, Identification and subcellular localization of the proteins encoded by the hepatitis C viral genome", Journal of General Virology, (1993), vol. 74, pp. 1103–1113.

Middaugh, et al., "The Effect of Temperature on Ribose–5–phosphate Isomerase from a Mesophile, *Thiobacillus thioparus*, and a Thermophile, *Bacillus caldolyticus*", J. Biochem., (1976), vol. 79, pp. 1331–1344.

Lee, et al., "Thermal Stability of Proteins in the Presence of Poly(ethylene glycols)", Biochemistry, (1987), vol. 26, pp. 7813–7819.

Boyd, et al., "Use of Polyvinyl Alcohol as a Stabilizer of Peroxidase–Antibody Conjugate for Enzyme Immunoassay", Biotechnology Techniques (1994), vol. 8, pp. 123–128.

Cleland, et al., "Polyethylene Glycol Enhanced Protein Refolding", Bio/Technology, (1992), vol. 10, pp. 1013–1019.

Fiore, et al., "The Abbott IMx™ Automated Benchtop Immunochemistry Analyzer System", Clinical Chemistry, (1988), vol. 34, pp. 1726–1732.

Nedjar-Arroume, et al., "Stabilizing effect of water/alcohol solvents towards autoxidation of human haemoglobin", Biotechnol. Appl. Biochem., (1993), vol. 18, pp. 25–35.

Mathews and Van Holde, Biochemistry, Benjamin/Cummings, Redwood City, CA, 1990, pp. 157–158.

Kuroki et al., Monoclonal antibodies against human pulmonary surfactant apo–proteins: specificity and application in immunochemistry; Biochim. Biophys. Acta 836, 201–209 (1985).

Gray, Additives and Enzyme Stability, Biocatalysis, 1, 187–196 (1988).

Sober, Handbook of Biochemistry, Selected Data for Molecular Biology Chemical Rubber Co., Cleveland, OH, 1968 pp. J–248–J–251.

*Primary Examiner*—Michael P. Woodward
*Assistant Examiner*—Henry E. Auer
*Attorney, Agent, or Firm*—David L. Weinstein

[57] ABSTRACT

An aqueous composition suitable for use when performing immunological procedures. The composition includes at least one biological buffer, dithiothreitol (alternatively referred to herein as "DTT"), and ethylene glycol. The composition can also include at least one biological detergent, at least one source of positive and negative counterions, e.g., salt, and at least one viscosity modifier, e.g., sugar. The buffer also can include at least one preservative, such as sodium azide. The pH of the composition preferably ranges from about 6.4 to 7.2. A kit containing the composition is also disclosed.

24 Claims, 1 Drawing Sheet

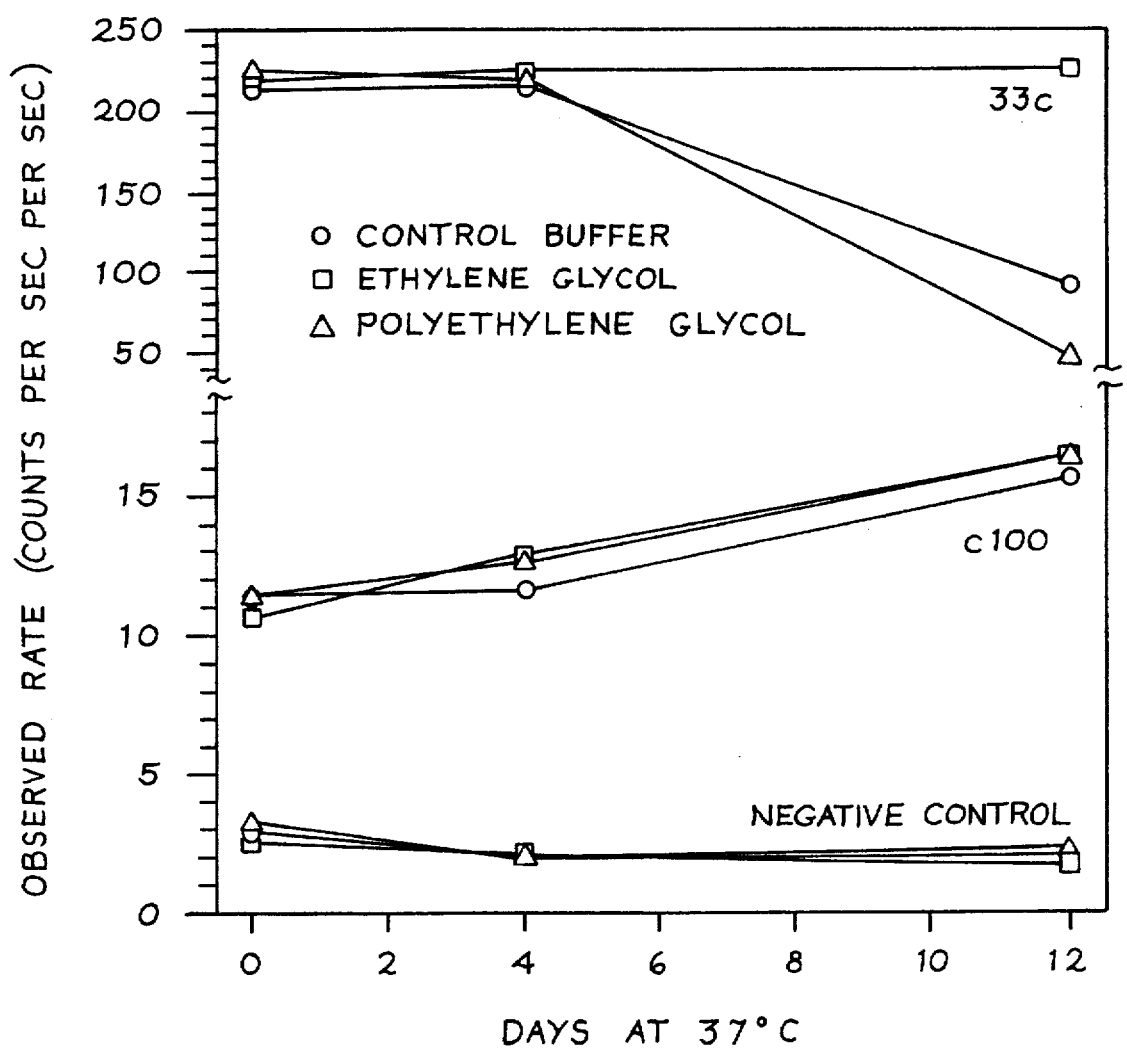

BUFFER COMPOSITION FOR REAGENTS FOR IMMUNOASSAY

BACKGROUND OF THE INVENTION

1. Field of the Invention

This invention relates to buffering compositions, and more particularly, to buffering compositions useful for immunological and immunochemical assay components, such as antibodies and antigens.

2. Discussion of the art

Many types of immunoassays can be run on an apparatus of the type described in U.S. Pat. No. 5,358,691, incorporated herein by reference. In general, immunoassays can be classified into two major categories—homogeneous and heterogeneous. Homogeneous and heterogeneous immunoassays depend upon the ability of a first binding member of a binding member pair, e.g., an antigen, to specifically bind to a second binding member of a binding member pair, e.g., an antibody. A conjugate, comprising one of such binding members labeled with a detectable moiety, is employed to determine the extent of such binding. For example, such binding member pairs can be an antigen and an antibody to such antigen. The conjugate, which can comprise the antigen, either participates in a binding reaction with the antibody or does not participate in such a reaction. The amount of detectable moiety detected and measured after the reaction can be correlated to the amount of antibody present in the test sample.

Heterogeneous assays can be performed in a competitive immunoassay format or in a sandwich immunoassay format. In the competitive immunoassay format, an antigen can be immobilized to a solid phase material whereby the amount of detectable moiety that is bound to a solid phase material can be detected, measured, and correlated to the amount of antibody present in the test sample. Examples of solid phase materials include beads, particles, microparticles, and the like. In the sandwich immunoassay format, a test sample containing, for example, an antibody is contacted with a protein such as an antigen. The antigen is immobilized on a solid phase material. Examples of solid phase materials include beads, particles, microparticles, and the like. The solid phase material is typically treated with a second antigen or antibody that has been labeled with a detectable moiety. The second antigen or antibody then becomes bound to the corresponding antigen or antibody on the solid phase material and, after one or more washing steps to remove any unbound material, an indicator material, such as a chromogenic substance, is introduced to react with the detectable moiety to produce a detectable signal, e.g., a color change. The color change is then detected, measured, and correlated to the amount of antibody present in the test sample. It should also be noted that various diluents and buffers are also required to optimize the operation of the microparticles, antigens, conjugates, and other components of the assay that participate in chemical reactions.

A heterogeneous immunoassay that can be performed with the apparatus of U.S. Pat. No. 5,358,691 in either a competitive or sandwich immunoassay format is a microparticle capture enzyme immunoassay, such as that described in *Clinical Chemistry*, Volume 34, No. 9, pages 1726–1732 (1988), employing microparticles as the solid phase material. This article is incorporated herein by reference.

A step-by-step description of a microparticle capture enzyme immunoassay procedure is set forth at col. 35, line 60 through col. 44, line 22 of U.S. Pat. No. 5,358,691.

Various components of of kits used in immunoassays run on the apparatus described in U.S. Pat. No. 5,358,691 must fulfill certain functional requirements. The microparticles must provide a solid phase for antibody capture, serving as a support for the antigens used for said capture. These particles must themselves be captured, e.g., by a matrix cell filter, to permit detection of bound antibody by the conjugate/substrate combination. The microparticle diluent must provide a medium that maintains the antigens' ability to be recognized by complementary antibodies in patient specimens (stability) while not inhibiting that recognition (signal generation). The conjugate must provide a means to specifically recognize antibodies bound to antigens on the microparticle and a means to generate a signal to indicate the presence of conjugate on the microparticle. The conjugate diluent must provide a medium that preserves and optimizes the ability of one binding pair member on the conjugate to recognize its complementary binding pair member, while simultaneously preserving and optimizing the ability of the enzyme portion, e.g., alkaline phosphatase portion, to hydrolyze the substrate into a detectable entity. In addition, the conjugate diluent must contain components that will minimize, if not eliminate, nonspecific binding of the conjugate to the matrix or microparticle, thus preventing the generation of a false signal. The sample dilution buffer must provide a medium that optimizes the ability of antibodies in a specimen to bind to antigen on the microparticles while preventing nonspecific interactions that might lead to the generation of a false signal Because certain antigens used in immunoassays are unstable after prolonged exposure to heat, it would be desirable to increase the stability of antigens to heat stress. Because antigens are characterized by certain epitopes, it would be desirable to increase the stability of the antigens by increasing the stability of the characteristic epitopes.

SUMMARY OF THE INVENTION

The present invention provides an aqueous composition suitable for use as a buffer, which composition comprises at least one biological buffer, dithiothreitol (alternatively referred to herein as "DTT"), and ethylene glycol. The medium of the composition is water. The composition can also include at least one biological detergent, at least one source of positive and negative counterions, e.g., salt, and at least one viscosity modifier, e.g., sugar. The buffer also can include at least one preservative, e.g., sodium azide. The pH of the composition of the present invention can range from about 6.4 to about 7.2, preferably from about 6.4 to about 6.8, more preferably from about 6.5 to about 6.7. Most preferably, the pH of the composition is about 6.6.

The composition is particularly useful for stabilizing the immunoreactivity of antigens, e.g., hepatitis C virus (HCV) antigens of the NS3 region of the viral genome, under heat stress conditions, in particular, temperatures ranging from 31° to 37° C. The composition of this invention has been found to be useful as a diluent for microparticles for diagnostic assays in which antigens are passively coated onto polymeric microparticles. It has been found that the use of ethylene glycol significantly enhances the long-term ability of antigens to detect complementary antibodies that bind to the antigens disposed on the surface of a microparticle.

The composition of this invention provides immunoreactive stability to antigens and antibodies at elevated temperatures, e.g., 37° C., for relatively long periods of time, e.g., 20 days.

In another aspect of the invention, a kit containing the composition as a component is also provided.

BRIEF DESCRIPTION OF THE DRAWING

FIG. 1 is a graph illustrating the advantageous effect of ethylene glycol upon the stability of 33c antigen, as evidenced by the ability to detect binding of anti-HCV antibodies to microparticles having 33c antigen coated thereon. The

DETAILED DESCRIPTION OF THE INVENTION

This invention involves an aqueous composition that is particularly useful for improving stability of antigens and antibodies under heat stress conditions. The composition comprises the following ingredients: at least one a b ical buffer, dithiothreitol [$HSCH_2(CHOH)_2CH_2SH$], and ethylene glycol [$HOCH_2CH_2OH$]. The medium of the composition is water.

In the preferred embodiments of the invention, the composition further includes at least one biological detergent, at least one source of positive and negative counterions, e.g., salt, at least one viscosity modifier, e.g., sugar. A preservative, e.g., sodium azide, can also be added to the composition to reduce microbial growth. The composition has a pH ranging from about 6.4 to about 7.2, more preferably from about 6.5 to about 6.7. If necessary, the pH of the composition can be adjusted with acid or base.

The function of the biological buffer is to maintain the pH of the medium at a constant level. It has been found that optimum results are obtained when the pKa of the buffer is within 1.0 pH unit of pH 6.6. In other words, the pKa of the buffer preferably ranges from 5.6 to 7.6.

Biological buffers that are suitable for the composition of the invention include, but are not limited to, the following acids or bases:

benzene-1,2,4,5-tetracarboxylic (pyromellitic)
benzene-1,2,3-tricarboxylic (hemimellitic)
dimethylmalonic
histidine
hydroxylamine
carbonic ($H_2CO_3$+$CO_2$)
malonic
2-(N-morpholino)-ethane sulfonic acid "MES"
glycerophosphoric
propane-1,2,3-tricarboxylic (tricarballylic)
benzenepentacarboxylic
maleic
2,2-dimethylsuccinic
ethylenediaminetetraacetic acid "EDTA"
3,3-dimethylglutaric
bis(2-hydoxyethyl)imino-tris(hydroxymethyl)methane "BIS-TRIS"
benzenehexacarboxylic (mellitic)
N-(2-acetamido)imino-diacetic acid "ADA"
butane-1,2,3,4-tetracarboxylic
pyrophosphoric
1,1-cyclopentanediacetic (3,3 tetramethylene-glutaric acid)
1,4-piperazinebis-(ethanesulfonic acid) "PIPES"
N-(2-acetamido)-2-aminoethanesulfonic acid "ACES"
1,1 -cyclohexanediacetic
3,6-endomethylene-1,2,3,6-tetrahydrophthalic acid "EMTA" ("ENDCA")
imidazole
2-(aminoethyl)trimethylammonium chloride "CHOLAMINE"
N,N-bis(2-hydroxyethyl)-2-aminoethanesulfonic acid "BES"
2-methylpropane-1,2,3-triscarboxylic (β-methyltricarballylic)
2-(N-morpholino)propane-sulfonic acid "MOPS"
phosphoric
N-tris(hydroxymethyi)methyl-2-aminoethane sulfonic acid "TES"
N-2-hydroxyethylpiperazine-N'-2-ethanesulfonic acid "HEPES"

In the foregoing list, the name of the compound in parentheses is the common name of the compound that precedes the name of the compound in parentheses. The acronym set off by quotation marks is the name of the compound commonly used when ordering the compound that precedes the acronym set off by quotation marks.

The buffer should be present in an amount sufficient to carry out its intended function, i.e., maintenance of the desired pH. Effective concentrations of the biological buffer can range from about 10 millimoles per liter to about 500 millimoles per liter (mM), more preferably from about 10 mM to about 100 mM. The preferred buffer is the buffer that goes by the acronym "MES".

The function of the dithiothreitol is to protect sulfhydryl groups in a protein. By protecting sulfhydryl groups in a protein, dithiothreitol allows the antigens, e.g., antigens of HCV, to retain their characteristic structure, thereby allowing recognition of antigens by their complementary antibodies. Dithiothreitol is described in detail in the brochure entitled "Cleland's Reagent", published by Calbiochem-Novabiochem Corporation, San Diego, Calif., incorporated herein by reference. As used herein, the term "dithiothreitol" includes both dithiothreitol and its isomer dithioerythritol. The dithiothreitol should be present in an amount sufficient to carry out its intended function, i.e., to protect sulfhydryl groups in a protein. As used herein, "protect sulfhydryl groups" means to repress oxidation of sulfhydryl groups in a protein to disulfide groups while not affecting disulfide groups already present in the protein groups. Effective concentrations of the dithiothreitol can range from about 2 millimoles per liter to about 10 millimoles per liter (mM), preferably from about 5 mM to about 10 mM, and more preferably about 10 mM.

The function of ethylene glycol is to prevent dithiothreitol from oxidation by oxidizing agents. For example, in the absence of ethylene glycol, dithiothreitol will be oxidized, thereby rendering dithiothreitol less effective for protecting sulfhydryl groups. Ethylene glycol is a 1,2-diol. Ethylene glycol was found to be superior to similar polyhydic alcohols or polymers, such as glycerol, polyethylene glycol, and polyvinyl acetate, with respect to the ability to preserve the binding capacity of antibodies, e.g., anti-HCV antibodies, to antigens. e.g., HCV antigens. Ethylene glycol should be present in an amount sufficient to protect dithiothreitol from oxidation. Effective concentrations of the ethylene glycol can range from about 4% to about 8%, preferably from about 4% to about 5%, and more preferably about 4%, based on weight per unit volume (g/100 ml).

It is highly desirable to include at least one biological detergent, at least one source of positive and negative counterions, e.g., a salt, and at least one viscosity modifier, e.g., a sugar in the composition of this invention in order to carry out effective immunoassays.

One function of the biological detergent (surfactant) is to reduce non-specific binding of antibodies other than the analyte antibodies, e.g., anti-HCV antibodies, to the microparticles. In other words, antibodies other than the analyte antibodies may adhere to the solid phase in the immunoassay for reasons other than the specific recognition of their complementary antigen. This non-specific binding is undesirable as it leads to false positive results. Biological detergents reduce the incidence of such binding caused by nonpolar or hydrophobic interactions.

Biological detergents (surfactants) that are useful in the composition include non-ionic surfactants, anionic surfactants, zwitterionic surfactants, and cationic surfactants. Non-ionic detergents include polyoxyethylene sorbitan monolaurate ("TWEEN® 20"), polyoxyethylene sorbitan monooleate ("TWEEN® 80"), polyoxyethylene ethers ("TRITON®", "BRIJ®"), and octylphenol-ethylene oxide ("NONIDET®"). Anionic surfactants include caprylic acid, cholic acid, deoxycholic acid, glycocholic acid and sodium dodecyl sulfate. Zwitterionic surfactants include "CHAPS®" (3-[3-Cholamidopropyl)-dimethylammonio]-1propanesulfonate). Cationic detergents include cetylpyridinium chloride. It is preferred that non-ionic detergents be used for the reason that they are known to reduce non-specific binding while simultaneously not inhibiting specific binding. Effective concentrations of the biological detergent can vary from detergent to detergent, but can typically range from about 0.01% to about 1%, preferably about 0.01%, based on weight per unit volume (g/100 ml). The preferred detergent is Triton® X-100.

The function of the source of positive and negative counterions (cations and anions) is to reduce non-specific binding of antibodies other than the analyte antibodies, e.g., anti-HCV antibodies, to the microparticles. In other words, antibodies other than the analyte antibodies may adhere to the solid phase in the immunoassay for reasons other than the specific recognition of their complementary antigen. This non-specific binding is undesirable as it leads to false positive results. Positive and negative counterions reduce the incidence of such binding caused by ionic interactions.

Suitable sources of positive and negative counterions include salts. Salts that are useful in the composition include such salts as NaCl and KCl. Effective concentrations of the salt can range from about 0.05 moles per liter to about 0.5 moles per liter (M), preferably from about 0.1M to about 0.3M, and most preferably from about 0.15M to about 0.25M.

The function of the viscosity modifier is to increase the viscosity of a solution containing microparticles so that the microparticles more easily remainsuspended in the solution and can be inhibited from settling. The use viscosity modifier in a diluent for microparticles has been found to achieve neutral density of the microparticles. Achievement of neutral density entails the determination of the optimum concentration of viscosity modifier that will eliminate settling of the microparticles. The concentration of viscosity modifier required to achieve neutral density is assay specific and microparticle lot specific. The principle involves dissolving viscosity modifier in solution to increase the density of the diluent. When the density of the diluent and microparticles are equivalent, the microparticles will be in a suspended state. Suitable viscosity modifiers include sugars, thickeners, and other agents, such as, for example, metrizamide and metrizoic acid. Sugars that are useful in the composition include such sugars as sucrose, glucose, and mannitol. Effective concentrations of the sugar can range from about 5% to about 25%, preferably from about 7% to about 20%, and most preferably from about 10% to about 15%, based on weight per unit volume (g/100 ml).

The function of the preservative is to reduce microbial growth in the composition. Preservatives that are useful in the composition include sodium azide. Effective concentrations of the preservative can range from about 0.1% to about 1%, preferably from about 0.1% to about 0.5%, and most preferably from about 0.1% to about 0.2%, based on weight per unit volume (g/100 ml).

It is preferred that the pH of the composition be below 7.2, more preferably below 7.0, and most preferably from about 6.5 to about 6.7. It is preferred that the pH of the composition be below 7.2 because experimental evidence shows that the ability to maintain disulfide bonds in their reduced state rapidly disappears as the pH increases above 7.2, as evidenced by reduction of antigen stability.

In a preferred embodiment, the buffer of the present invention contains the following ingredients in the amounts indicated, wherein mM, M and % are as previously defined:

| Ingredient | Amount |
| --- | --- |
| Biological buffer | 10 mM to 100 mM |
| Biological detergent | 0.01% to 1% |
| Source of positive and negative counterions (salt) | 0.1M to 0.3M |
| Viscosity modifier (sugar) | 7% to 20% |
| Preservative | 0.1% to 0.5% |
| Dithiothreitol | 5 mM to 10 mM |
| Ethylene glycol | 4% to 5% |

The composition of the invention can be prepared simply by mixing the foregoing components in water in any order and taking care to ensure that the pH of the composition is adjusted to the proper level. The order of addition of ingredients is not critical.

The composition of the invention is useful as a diluent of assay components. The term "assay components", as used herein, means the solid phase that contains antigen for antibody capture, e.g., microparticles coated with antigen. In addition, assay components include commercial assay reagents such as polyclonal and/or monoclonal antibodies, particularly of IgG or IgM class, and fragments thereof; antigens and fragments thereof; antigenic lysates, recombinant proteins, synthetic peptides, and the like. It also is contemplated that inert assay materials, such as latex particles, magnetic beads, microparticles and the like, if provided in a suspension, may be suspended in the composition of the invention, or if dilution of these materials in a suspension is desired, the dilution may be performed with the composition of the invention.

The composition of the invention may be used to dilute assay components prior to performing the assay itself. The composition is especially useful for diluting antigens that are used in determining the presence or absence of specific antibodies to HCV. An example of such a method of dilution is described at col. 37, line 20 through col. 41, line 21 of U.S. Pat. No. 5,358,691.

In another aspect ot the invention, the composition can be provided as a component of a kit. As used herein, the term "kit" means a collection of reagents and associated materials, e.g., diluents, buffers, required to perform an assay. In the apparatus described in U.S. Pat. No. 5,358,691, a form of a kit is shown in FIGS. 4A and 4B. The kit is referred to as a reagent pack. The composition of this invention can be packaged in one of the receptacles of the reagent pack.

The following non-limiting examples will further illustrate the invention. In the examples, all concentrations are based on moles per liter (M), millimolesper liter (mM), or per cent (grams per 100 milliliters).

EXAMPLES

Example 1 and Comparative Examples A–D

This example illustrates the effect of a composition containing a biological buffer, dithiothreitol, and ethylene glycol on the stability of hepatitis C virus (HCV) antigen under heat stress conditions.

A stock composition containing biological buffer was prepared by combining the following ingredients to arrive at the indicated concentrations:

| Ingredient | Concentration |
| --- | --- |
| Biological buffer ("MES") | 10 mM |
| Biological detergent ("TRITON ® X-100) | 0.01% |
| Salt (NaCl) | 0.2M |
| Sugar (sucrose) | 11.5% |
| Preservative (sodium azide) | 0.1% |
| Dithiothreitol | 10 mM |

Each of the following additives was added to a separate portion of the stock composition to form four modified stock compositions. Each additive and the concentration thereof are set forth below:

| Example | Additive | Concentration |
| --- | --- | --- |
| 1 | Ethylene glycol | 5% |
| Comp. A | Polyethylene glycol | 1% |
| Comp. B | Polyvinyl alcohol | 1% |
| Comp. C | Glycerol | 5% |
| Comp. D | None | 0% |

Microparticles (polystyrene, 0.8 micrometer average diameter, commercially available from Seradyn) were coated with HCV antigens. The antigens were HC43/c100, c200, and NS5. The 33c antigen was present in both the HC34 antigen and the c200 antigen. One set of microparticles was coated with the HC43/c100 antigen. A second set of microparticles was coated with the c200 antigen. A third set of microparticles was coated with the NS5 antigen. Coating of the microparticles was carried out by passive adsorption. All three sets of the coated microparticles were blended together and a portion of the resulting blend was introduced into each of the four modified stock solutions (Example 1 and Comparative Examples A, B, and C) and into the unmodified stock solution, which acted as a control (Comparative Example D).

The microparticles were used to detect antibodies in single marker specimens used in assay development, specifically, panels containing anti-HCV antibodies to viral core, c100, or 33c antigens, as well as a negative control The negative control contained no antibodies. All tests were run in triplicate and averaged.

Each solution containing the coated microparticles was incubated for a period of approximately 12 days at each of the following temperatures:

2°–8° C.
31° C.
37° C.

The solution containing glycerol severely reduced signal generation in the assay. Accordingly, this solution was not evaluated beyond the fourth day. The solution containing polyvinyl acetate also reduced signal generation in the assay. Accordingly, this solution was not evaluated beyond the fourth day. The solutions containing glycol and polyethylene glycol and the control were maintained at their respective temperatures and tested on the twelfth day.

The assay employed to test the effect of the additives was a microparticle capture enzyme immunoassay, was similar to that described in U.S. Pat. No. 5,358,691, wherein the enzyme was alkaline phosphatase and the enzyme substrate was 4-methylumbelliferyl phosphate. However, in this assay, the antigens were coated onto microparticles, the analyte in the test sample was anti-HCV antibody, and the enzyme was attached to anti-human IgG antibody to form the conjugate. The assay format was a sandwich assay wherein the antigen would bind to the anti-HCV antibody, which, in turn, would bind to the conjugate.

FIG. 1 shows the results for the experiments carried out under the most extreme heat stress conditions (37° C. for 12 days). FIG. 1 shows results for antibodies to the c100 antigen, the 33c antigen, and the negative control.

The composition containing ethylene glycol showed superiority over the control and the composition containing polyethylene glycol with respect to maintaining detection of 33c activity following subjection to extreme heat stress conditions.

The antigens used in the assay are described below. Individual blood or plasma donors or patients (based on clinical evaluation) may be tested for antibodies to HCV. The presence of these antibodies indicates that the individual (donor or patient) has been infected with HCV, may harbor infectious HCV, and may be capable of transmitting non-A, non-B hepatitis (NANBH).

HC43

The recombinant HCV protein HC43, expressed in *E. coli*, contains sequences of putative HCV core structural protein and HCV nonstructural protein NS3. HC43 is a fusion protein consisting of amino acids 1 to 150 and 1192 to 1457 of the HCV polyprotein. The amino acids 1192 to 1457 of the HCV polyprotein constitute the 33c antigen.

c100-3

The recombinant HCV protein c100-3, expressed in *Saccharomyces cerevisiae* (yeast), contains sequences of the putative HCV nonstructural proteins NS3 and NS4. c100-3 is a chimeric fusion region of 154 amino acids of human superoxide dismutase (SOD), five linker amino acids, amino acids 1569 to 1931 of the HCV polyprotein and an additional five linker amino acids at the carboxyl c200

The recombinant HCV protein c200 expressed in yeast contains HCV amino 4 regions of the HCV genome. c200 is a chimeric fusion protein with 154 amino acids of superoxide dismutase (SOD).

NS5

The recombinant HCV protein NS5, expressed in yeast, contains sequences of the putative HCV nonstructural protein NS5. NS5 is a chimeric fusion region of 154 amino acids of SOD and amino acids 2054 to 2995 of the HCV polyprotein.

A more detailed discussion of the hepatitis C viral genome can be found in Selby et al., "Expression, identification and subcellular localization of the proteins encoded by the hepatitis C viral genome", *Journal of General Virology* (1993), 74, 1103–1113, incorporated herein by reference.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An aqueous composition suitable for stabilizing the immunoreactivity of hepatitis C virus antigens of the NS3 region of the viral genome under heat stress conditions, said composition comprising:

at least one biological buffer in a concentration sufficient to maintain the pH at a level below about 7.2;

dithiothreitol in a concentration sufficient to protect sulfhydryl groups of said hepatitis C virus antigens of the NS3 region of the viral genome under heat stress conditions; and ethylene glycol in a concentration sufficient to preserve the binding capacity of antibodies to said hepatitis C virus antigens of the NS3 region of the viral genome under heat stress condition; wherein said composition has a pH of below about 7.2.

2. The composition of claim 1 wherein said at least one biological buffer is present in a concentration ranging from about 10 mM to about 500 mM.

3. The composition of claim 1 wherein said at least one biological buffer is an acid or base selected from the group consisting of:

benzene-1,2,4,5-tetracarboxylic (pyromellitic);

benzene-1,2,3-tricarboxylic (hemimellitic);

dimethylmalonic;

histidine;

hydroxylamine;

carbonic ($H_2CO_3$+$CO_2$);

malonic;

2-(N-morpholino)-ethane sulfonic acid "MES";

glycerophosphoric;

propane-1,2,3-tricarboxylic (tricarballylic);

benzenepentacarboxylic;

maleic;

2,2-dimethylsuccinic;

ethyenediaminetetraacetic acid "EDTA";

3,3-dimethylglutaric;

bis(2-hydoxyethyl)imino-tris(hydroxymethyl)methane "BISTRIS";

benzenehexacarboxylic (mellitic);

N-(2-acetamido)imino-diacetic acid "ADA";

butane-1,2,3,4-tetracarbo xylic;

pyrophosphoric;

1,1-cyclopentanediacetic (3,3 tetramethylene-glutaric acid);

1,4-piperazinebis-(ethanesulfonic acid) "PIPES";

N-(2-acetamido)-2-aminoethanesulfonic acid "ACES";

1,1-cyclohexanediacetic;

3,6-endomethylene-1,2,3,6-tetrahydrophthalic acid "EMTA"("ENDCA");

imidazole;

2-(aminoethyl)trimethylammonium chloride "CHOLAMINE";

N,N-bis(2-hydroxyethyl)-2-aminoethanesulfonic acid "BES";

2-methylpropane-1,2,3-triscarboxylic (β-methyltricarballylic);

2-(N-morpholino)propane-sulfonic acid "MOPS";

phosphoric;

N-tris(hydroxymethyl)methyl-2-aminoethane sulfonic acid "TES"; and

N-2-hydroxyethylpiperazine-N'-2-ethanesulfonic acid "HEPES".

4. The composition of claim 1 wherein said at least one biological buffer has a pKa ranging from about 5.6 to about 7.6.

5. The composition of claim 1 wherein dithiothreitol is present in a concentration ranging from about 2 mM to about 10 mM.

6. The composition of claim 1 wherein ethylene glycol is present in a concentration ranging from about 4% to about 8%, wherein % means g/100 ml.

7. The composition of claim 1 further including at least one biological detergent in a concentration sufficient to reduce non-specific binding of antibodies other than anti-HCV antibodies to HCV antigen caused by non-ionic interactions.

8. The composition of claim 7 wherein said at least one biological detergent is present in a concentration ranging from about 0.01% to about 1%, wherein % means g/100 ml.

9. The composition of claim 7 wherein said at least one biological detergent is selected from the group consisting of non-ionic surfactants, anionic surfactants, zwitterionic surfactants, and cationic surfactants.

10. The composition of claim 9 wherein said at least one biological detergent is a non-ionic surfactant.

11. The composition of claim 10 further comprising an anionic surfactant.

12. The composition of claim 1 further including at least one source of positive and negative counterions in a concentration sufficient to reduce non-specific binding of antibodies other than anti-HCV antibodies to HCV antigen caused by ionic interactions.

13. The composition of claim 12 wherein said at least one source of positive and negative counterions is present in a concentration ranging from about 0.05M to about 0.5M.

14. The composition of claim 12 wherein said at least one source of positive and negative counterions is a salt.

15. The composition of claim 14 wherein said salt is selected from the group consisting of NaCl and KCl.

16. The composition of claim 1 further including at least one viscosity modifier in a concentration sufficient to increase viscosity of a solution containing microparticles suspended therein so that settling of said microparticles suspended therein will be reduced.

17. The composition of claim 16 wherein said at least one viscosity modifier is present in a concentration ranging from about 5% to about 25%, wherein % means g/100 ml.

18. The composition of claim 16 wherein said at least one viscosity modifier is a sugar.

19. The composition of claim 18 wherein said sugar is selected from the group consisting of sucrose, glucose, and mannitol.

20. The composition of claim 1 further including at least one preservative in a concentration sufficient to reduce microbial growth.

21. The composition of claim 20 wherein said at least one preservative is present in a concentration ranging from about 0.1% to about 1.0%, wherein % means g/100 ml.

22. The composition of claim 20 wherein said at least one preservative is sodium azide.

23. The composition of claim 1 wherein said composition has a pH ranging from about 6.4 to about 6.8.

24. An aqueous composition suitable for stabilizing the immunoreactivity of hepatitis C virus antigens of the NS3 region of the viral genome under heat stress conditions, said composition comprising:

at least one biological buffer in a concentration in the range of from about 10 mM to about 500 mM;

dithiothreitol in a concentration in the range of from about 2 mM to about 10 mM;

ethylene glycol in a concentration in the range of from about 4% to about 8%;

at least one biological detergent in a concentration in the range of from about 0.01% to about 1%;

at least one source of positive and negative counterions in a concentration in the range of from about 0.05M to about 0.5M;

at least one viscosity modifier in a concentration in the range of from about 5% to about 25%; and at least one preservative in a concentration in the range of from about 0.1% to about 1%;

wherein said composition has a pH in the range of from about 6.4 to about 7.2, and wherein % means g/100 ml, said composition capable of stabilizing the immunoreactivity of hepatitis C virus antigens of the NS3 region of the viral genome under heat stress conditions.

* * * * *

UNITED STATES PATENT AND TRADEMARK OFFICE
CERTIFICATE OF CORRECTION

PATENT NO. : 5,616,460
DATED : April 1, 1997
INVENTOR(S) : Figard

It is certified that error appears in the above-indentified patent and that said Letters Patent is hereby corrected as shown below:

Column 9, line 62, change "tetracarbo xylic" to --tetracarboxylic--.

Signed and Sealed this

Fifth Day of August, 1997

*Attest:*

BRUCE LEHMAN

*Attesting Officer*       *Commissioner of Patents and Trademarks*